(12) United States Patent
Chen et al.

(10) Patent No.: US 8,791,056 B2
(45) Date of Patent: Jul. 29, 2014

(54) ALKYLPHOSPHOROFLUORIDOTHIOATES HAVING LOW WEAR VOLUME AND METHODS FOR SYNTHESIZING AND USING SAME

(75) Inventors: Xin Chen, Dallas, TX (US); Pranesh B. Aswath, Grapevine, TX (US); Ronald L. Elsenbaumer, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 136 days.

(21) Appl. No.: 13/168,478

(22) Filed: Jun. 24, 2011

(65) Prior Publication Data

US 2011/0319303 A1    Dec. 29, 2011

Related U.S. Application Data (60) Provisional application No. 61/358,090, filed on Jun. 24, 2010.

(51) Int. Cl.
*C07F 9/20* (2006.01)
*C10M 137/10* (2006.01)

(52) U.S. Cl.
USPC ........................................................ 508/427

(58) Field of Classification Search
USPC ........................................................ 508/427
See application file for complete search history.

(56) References Cited

U.S. PATENT DOCUMENTS

| | | | |
|---|---|---|---|
| 2,167,784 A | 8/1939 | Svendsen | |
| 2,230,654 A | 1/1941 | Plunkett | |
| 2,510,112 A | 6/1950 | Holbrook | |
| 2,624,713 A | 1/1953 | Hurley | |
| 2,884,431 A | 4/1959 | Smith et al. | |
| 2,904,398 A | 9/1959 | Smith | |
| 2,924,508 A | 2/1960 | Gililand et al. | |
| 2,952,514 A | 9/1960 | Smith | |
| 2,959,544 A * | 11/1960 | Smith, Jr. et al. | 508/371 |
| 2,993,567 A | 7/1961 | Schachner | |
| 3,097,063 A | 7/1963 | Gililand et al. | |
| 3,194,762 A | 7/1965 | Browning et al. | |
| 3,247,116 A | 4/1966 | Relling | |
| 3,314,889 A | 4/1967 | Christian | |
| 3,432,431 A | 3/1969 | Mitacek | |
| 3,493,513 A | 2/1970 | Petriello | |
| 3,505,229 A | 4/1970 | Skehan | |
| 3,536,624 A | 10/1970 | Christian et al. | |
| 3,565,700 A | 2/1971 | Root | |

(Continued)

FOREIGN PATENT DOCUMENTS

| | | |
|---|---|---|
| EP | 0856570 | 8/1998 |
| GB | 804777 | 11/1958 |
| JP | 10287402 | 10/1998 |

OTHER PUBLICATIONS

Parekh et al., Synthesis of Fluorinated ZDDP Compounds, Oct. 15, 2008.*

(Continued)

*Primary Examiner* — Taiwo Oladapo
(74) *Attorney, Agent, or Firm* — Parks IP Law LLC; Collen A. Beard, Esq.

(57) ABSTRACT

Alkylphosphorofluoridothioates containing alkyl groups of greater than four carbons which exhibit significantly lower wear volume compared to ZDDP, methods of making same with high yields, and methods of using same as lubricant additives.

17 Claims, 11 Drawing Sheets

(56) References Cited

U.S. PATENT DOCUMENTS

| | | |
|---|---|---|
| 3,567,521 A | 3/1971 | Toy et al. |
| 3,592,700 A | 7/1971 | Toy |
| 3,607,747 A | 9/1971 | Ishikawa |
| 3,636,172 A | 1/1972 | Gardner |
| 3,640,859 A | 2/1972 | Messina et al. |
| 3,720,722 A | 3/1973 | Wada et al. |
| 3,723,317 A | 3/1973 | Ulery |
| 3,750,911 A | 8/1973 | Ebner et al. |
| 3,806,455 A | 4/1974 | Siegart et al. |
| 3,909,431 A | 9/1975 | Figiel |
| 3,933,656 A | 1/1976 | Reick |
| 3,969,233 A | 7/1976 | Lucas |
| 4,012,493 A | 3/1977 | Layne et al. |
| 4,021,530 A | 5/1977 | Layne et al. |
| 4,029,870 A | 6/1977 | Brown et al. |
| 4,034,070 A | 7/1977 | Wojtowicz et al. |
| 4,036,718 A | 7/1977 | Brown et al. |
| 4,052,323 A | 10/1977 | Feneberger et al. |
| 4,127,491 A | 11/1978 | Reick |
| 4,130,492 A | 12/1978 | Longo et al. |
| 4,224,173 A | 9/1980 | Reick |
| 4,252,678 A | 2/1981 | Smith |
| 4,313,761 A | 2/1982 | Joyce et al. |
| 4,349,444 A | 9/1982 | Reick |
| 4,363,737 A | 12/1982 | Rodriguez |
| 4,405,469 A | 9/1983 | Hafner |
| 4,465,607 A | 8/1984 | Cottell |
| 4,484,954 A | 11/1984 | Tarancon |
| 4,500,678 A | 2/1985 | Kita et al. |
| 4,545,964 A | 10/1985 | Bergez et al. |
| 4,584,116 A | 4/1986 | Hermant et al. |
| 4,615,917 A | 10/1986 | Runge |
| 4,638,444 A | 1/1987 | Laragione et al. |
| 4,657,687 A | 4/1987 | Caporiccio et al. |
| 4,741,893 A | 5/1988 | Watanabe et al. |
| 4,764,056 A | 8/1988 | Zentgraf et al. |
| 4,770,797 A | 9/1988 | Syracuse et al. |
| 4,803,005 A | 2/1989 | Juhlke et al. |
| 4,824,690 A | 4/1989 | Heinecke et al. |
| 4,832,859 A | 5/1989 | Basset et al. |
| 4,834,894 A | 5/1989 | Scheld |
| 4,857,294 A | 8/1989 | Bridenne Alaux et al. |
| 4,857,492 A | 8/1989 | Bradley et al. |
| 4,859,357 A | 8/1989 | Germanaud et al. |
| 4,888,122 A | 12/1989 | McCready |
| 4,892,669 A | 1/1990 | Marcora et al. |
| 4,917,872 A | 4/1990 | Nakahara et al. |
| 4,938,945 A | 7/1990 | Mahmood et al. |
| 4,983,373 A | 1/1991 | Withers, Jr. et al. |
| 5,004,554 A | 4/1991 | Tohzuka et al. |
| 5,009,963 A | 4/1991 | Ohmi et al. |
| 5,096,145 A | 3/1992 | Phillips et al. |
| 5,110,657 A | 5/1992 | Ainslie |
| 5,116,900 A | 5/1992 | Flautt et al. |
| 5,118,434 A | 6/1992 | Meyer et al. |
| 5,133,886 A | 7/1992 | Hata |
| 5,160,646 A | 11/1992 | Scheld |
| 5,188,747 A | 2/1993 | Kai et al. |
| 5,227,081 A | 7/1993 | Sawa et al. |
| 5,242,506 A | 9/1993 | Barber et al. |
| 5,286,882 A | 2/1994 | Zuzich et al. |
| 5,350,727 A | 9/1994 | Tsurumi et al. |
| 5,373,986 A | 12/1994 | Rafferty et al. |
| 5,380,557 A | 1/1995 | Spiro |
| 5,385,683 A | 1/1995 | Ransom |
| 5,447,896 A | 9/1995 | Rao |
| 5,460,661 A | 10/1995 | Maynard, Jr. |
| 5,595,962 A | 1/1997 | Caporiccio et al. |
| 5,641,731 A | 6/1997 | Baumgart et al. |
| 5,698,483 A | 12/1997 | Ong et al. |
| 5,767,045 A | 6/1998 | Ryan |
| 5,877,128 A | 3/1999 | Greer |
| 6,045,692 A | 4/2000 | Bilski et al. |
| 6,080,899 A | 6/2000 | Bradley et al. |
| 6,152,978 A | 11/2000 | Lundquist |
| 6,258,758 B1 | 7/2001 | Greer |
| 6,316,377 B1 | 11/2001 | Fulton et al. |
| 6,361,678 B1 | 3/2002 | Childs et al. |
| 6,362,135 B1 | 3/2002 | Greer |
| 6,413,918 B1 | 7/2002 | Beatty et al. |
| 6,436,362 B1 | 8/2002 | Cuzzato |
| 6,541,430 B1 | 4/2003 | Beatty |
| 6,630,610 B2 | 10/2003 | Swain et al. |
| 6,642,186 B2 | 11/2003 | Beatty et al. |
| 6,734,320 B2 | 5/2004 | Beatty et al. |
| 6,764,984 B2 | 7/2004 | Beatty |
| 6,835,218 B1 | 12/2004 | Drozd et al. |
| 6,955,793 B1 | 10/2005 | Arencibia et al. |
| 6,960,555 B2 | 11/2005 | Anthony et al. |
| 7,074,745 B2 | 7/2006 | Shaub et al. |
| 7,592,287 B2 | 9/2009 | Kemnitz et al. |
| 7,754,662 B2 | 7/2010 | Aswath et al. |
| 7,879,776 B2 | 2/2011 | Patel et al. |
| 2001/0038048 A1 | 11/2001 | Blanton |
| 2003/0125561 A1* | 7/2003 | Carpino et al. ............ 546/268.1 |
| 2003/0139300 A1 | 7/2003 | Beatty |
| 2005/0119135 A1 | 6/2005 | Shaub et al. |
| 2006/0014652 A1 | 1/2006 | Parekh et al. |
| 2006/0040832 A1 | 2/2006 | Zhang |
| 2006/0063683 A1 | 3/2006 | Parekh et al. |
| 2006/0281644 A1* | 12/2006 | Aswath et al. ............ 508/369 |
| 2007/0093397 A1 | 4/2007 | Patel et al. |

OTHER PUBLICATIONS

Parekh et al, "Synthesis of Fluorinated ZDDP Compounds", Tribol Lett, 34:141-153 (2009).
Kirk-Othmer "Concise Encyclopedia of Chemical Technology", John Wiley & Sons, Inc., pp. 37 and 292-297 (1985).
Howe-Grant et al. "Fluorine Chemistry: A Comprehensive Treatment", John Wiley & Sons, Inc., pp. 115-138 (1995).
Parker, S. "McGraw-Hill Encyclopedia of Chemistry", McGraw-Hill, 2nd ed, pp. 507-508 (1993).
Lide, D "CRC Handbook of Chemistry and Physics", CRC Press, Inc., 75th ed, pp. 5-1-5-23 (1995).
"Hydrofluoric Acid Properties", Honeywell, vol. 1.0, p. 26 (2000).

* cited by examiner

FIGURE 11

ALKYLPHOSPHOROFLUORIDOTHIOATES HAVING LOW WEAR VOLUME AND METHODS FOR SYNTHESIZING AND USING SAME

BACKGROUND OF THE INVENTION

The present application relates generally to lubricants and, more particularly, to improving the quality of lubricants through the addition of high performance lubricant additives that enhance desirable properties of lubricants.

Commercial lubricants are compositions containing a lubricant base such as a hydrocarbon base oil or base grease (oil to which a thickener has been added to form a semi-solid or gel), to which are added various lubricant additives selected for additional desirable properties. Lubricant additives may enhance the lubricity of the lubricant base and/or may provide antiwear, antifriction, or other desirable characteristics.

Lubricants are used in enormous quantities. For example, more than four billion quarts of crankcase oil are used in the United States per year. However, many lubricants currently in use have undesirable side effects. Currently available crankcase oils generally include the anti-wear additive zinc dialkyldithiophosphate (ZDDP), which contains phosphorous and sulfur. This phosphorous and sulfur ends up in the exhaust gas and poisons the catalytic converter causing increased automotive emissions. It is expected that the automotive industry will eventually mandate the total elimination of phosphorous and/or sulfur components in lubricants or will allow only extremely low levels of phosphorous and/or sulfur in crankcase oil. In addition, ZDDP produces ash (inorganic oxides that can be abrasive) due to the presence of zinc. However, no acceptable anti-wear additive to replace ZDDP in engine oils is currently available and thus it is still used, although desirably in smaller amounts.

Accordingly, it is an object of the present invention to provide environmentally friendly anti-wear additives for lubricants, wherein the amounts of phosphorous and sulfur which are contributed by the anti-wear additive to the lubricant are reduced. It is another object of the present invention to provide additives that produce little to no ash content from metal oxide production on combustion. It is yet another objective of the present invention to provide additives with desirable antiwear and antifriction characteristics.

A new class of materials called alkylphosphorofluoridothioates have been developed that exhibit superior wear protection compared to the current additive ZDDP. These materials are ashless because they do not contain metallic elements. In addition, these alkylphosphorofluoridothioates can be used at much lower levels of phosphorous content compared to ZDDP resulting in decreased fouling of the catalytic converters in automobiles and resulting in lower emissions. There is also the potential to reduce friction in the engine resulting in improved fuel economy compared to current additives in the marketplace.

Fluorothiophosphates are disclosed in US Patent Application No. 20060281644, for example. These fluorothiophosphates are produced by reacting a metal fluoride with an organothiophosphate such as ZDDP, yielding a fluorinated organothiophosphate. The reacting step involves heating and milling the reactants. The fluoride displaces one of the sulfur atoms in the reaction.

The present invention is a facile method for preparing alkylphosphorofluoridothioates and an improvement over the additives taught in US Patent Application No. 20060281644 and related applications. The present invention further comprises novel alkylphosphorofluoridothioates, methods of using same as lubricant additives, and lubricants containing the same.

SUMMARY OF THE INVENTION

In one aspect, the present invention is directed to a method of making ashless alkylphosphorofluoridothioates which provides a very high yield. The method involves a first reaction of a phosphorus pentasulfide with appropriate alcohols. A second reaction turns the O,O-dialkyl dithiophosphoric acid produced in the first reaction into the alkylphosphorofluoridothioate.

The invention is further directed to alkylphosphorofluoridothioates wherein the alkyl groups have greater than four carbons and exhibit significantly lower wear volume compared to ZDDP of the same phosphorus content.

The invention is further directed to methods of using alkylphosphorofluoridothioates wherein the alkyl groups have greater than four carbons as lubricant additives. In one embodiment the additives are used in motor oils in combination with a base oil and optionally other additives. In one embodiment, the alkylphosphorofluoridothioates are used in combination with ZDDP in an amount of about 5%-50% alkylphosphorofluoridothioates.

DETAILED DESCRIPTION OF THE INVENTION

The present invention is directed to novel alkylphosphorofluoridothioates having the formula where $R_1$ and $R_2$ are the same or different and are alkyl groups of greater than four carbons and up to as many as 40 carbons. Preferably the alkyl groups have between 5 and 22 carbons. Alkylphosphorofluoridothioates with larger alkyl groups will be solids and are applicable for use with solid lubricants such as greases.

The present invention is also directed to a method of making alkylphosphorofluoridothioates which provides nearly a 100% yield. The method involves a first reaction of a phosphorus pentasulfide with appropriate alcohols. A second reaction turns the O,O-dialkyl dithiophosphoric acid produced in the first reaction into the alkylphosphorofluoridothioate.

The compounds can be used as lubricant additives. They exhibit significantly lower wear volume compared to ZDDP, are ashless, and can be used at lower levels of phosphorous. In addition, the alkylphosphorofluoridothioates have 50% lower sulfur levels compared to ZDDP because the alkylphosphorofluoridothioates have one sulfur atom for every one phosphorous atom while ZDDP has two sulfur atoms for each phosphorous atom in the structure.

Typically liquid lubricants contain 90% base oil (most often petroleum fractions, called mineral oils) and about 10% additives. Vegetable oils or synthetic liquids such as hydrogenated polyolefins, esters, silicones, fluorocarbons, and many others are also sometimes used as base oils. Lubricants can be made with alkylphosphorofluoridothioates in amounts of from 1-10% in combination with a base oil. Additional additives can also be included in the lubricant. For example, antioxidants, detergents, viscosity modifiers, pour point depressants, corrosion inhibitors, and dispersants are also often included and make up the remainder of a fully formulated oil.

For motor oils, the amount of alkylphosphorofluoridothioate in the lubricant will generally be the amount that provides a phosphorous concentration of from about 0.01 to 0.15 wt % phosphorous. This generally correlates to between about 0.1 to 1.5 wt % of the alkylphosphorofluoridothioate. The amount of alkylphosphorofluoridothioate used will depend on the phosphorus concentration desired and the number of carbon atoms (which correlates to molecular weight) in the alkylphosphorofluoridothioate. Accordingly, alkylphosphorofluoridothioates with larger R groups (higher molecular weight) will be used in higher concentration for equivalent levels of phosphorus in the finished oil.

Selection of the alkylphosphorofluoridothioate to be used in the lubricant is thus based in part on desired phosphorus content and the molecular weight of the alkylphosphorofluoridothioate. It is also based on the thermal stability of the alkylphosphorofluoridothioate. Alkylphosphorofluoridothioates made with primary alcohols are more thermally stable than ones made from secondary alcohols. In addition, alkylphosphorofluoridothioates with longer chain alkyl groups are more thermally stable than ones with shorter chain alkyl groups. The various thermal stabilities of the compounds mean that there is quite a bit of capability to tailor the operative temperature range in which wear protection can be achieved as well as length of time for the wear protection (time-temperature profiles for wear protection).

The alkylphosphorofluoridothioates can be used in combination to achieve the performance profile that is desired. For example, in terms of temperature profile, additives having a low temperature decomposition (for early wear protection) can be mixed with additives having a higher temperature decomposition for longer time wear protection.

Further embodiments of the invention comprise lubricant additives and lubricants made by combining the alkylphosphorofluoridothioates of the invention with organophosphates such as zinc dialkyldithiophosphate (ZDDP), organofluorine compounds such as polytetrafluoroethylene (PTFE), ashless phosphates, and ashless thiophosphates. Mixtures of the alkylphosphorofluoridothioates with ZDDP exhibit superior wear performance compared to ZDDP alone and a unusual and unexpected synergistic antiwear effect is observed when the mixture comprises about 5%-50% alkylphosphorofluoridothioates.

Motor oils are described above. In applications such as greases the alkylphosphorofluoridothioates can be used in combination with organophosphates such as zinc dialkyldithiophosphate (ZDDP), ashless organothiophosphates, organofluorine compounds such as PTFE, and sulfurized olefins. The concentration of phosphorus in the grease can range from 0.01 wt % to as high as 0.5 wt %. In the case of greases the antiwear additives are mixed with base grease which is a mixture of mineral oil and soap thickener.

On the other hand, in the case of gear oils and transmission oils, the anti-wear additives could be a mixture of alkylphosphorofluoridothioates with organophosphates such as zinc dialkyldithiophosphate (ZDDP), ashless organothiophosphates, and PTFE. The concentration of phosphorus in transmission oils and gear oils preferably ranges from 0.01 wt % to as high as 0.3 wt %.

The examples below serve to further illustrate the invention, to provide those of ordinary skill in the art with a complete disclosure and description of how the compounds, compositions, articles, devices, and/or methods claimed herein are made and evaluated, and are not intended to limit the scope of the invention. In the examples, unless expressly stated otherwise, amounts and percentages are by weight, temperature is in degrees Celsius or is at ambient temperature, and pressure is at or near atmospheric.

EXAMPLE 1

Method for Making Alkylphosphorofluoridothioates

General Experimental Details

All of the reagents were purchased from commercial suppliers and were used without purification unless otherwise specified. Reactions involving air- or water-sensitive compounds were conducted in oven-dried (overnight) glassware under an atmosphere of dry argon. Anhydrous solvents were freshly prepared according to well documented methods. NMR spectra ($^1$H, $^{13}$C, $^{31}$P, and $^{19}$F) were recorded on JEOL eclipse+ instrument at 500, 125, 202 and 470 MHz respectively using $CDCl_3$ as solvent and TMS as reference unless otherwise noted. Melting points were obtained in capillary tubes on a MeI-Temp II apparatus, and the thermometer was uncorrected. Infrared (IR) spectra were obtained on a Bruker Vector 22 FT-IR spectrometer, using KBr pressed pellets for solids or neat films between KBr plates for liquids and oils, and are reported in $cm^{-1}$ with a resolution of 4 $cm^{-1}$. High resolution electrospray ionization time-of-flight (ESI-TOF) experiments were performed on an Agilent ESI-TOF mass spectrometer at Scripps Center for Mass Spectrometry (La Jolla, Calif. 92037). Sample was electrosprayed into the TOF reflectron analyzer at an ESI voltage of 4000V and a flow rate of 200 microliters/minutes. All column chromatography separations were performed on Sorbent Technologies silica gel (standard grade, 60 A, 32-63 μm).

General Synthetic Procedure

Preparation of O,O-dialkyl dithiophosphoric acids

To a vigorously stirred suspension of phosphorus pentasulfide (22.2 g, 0.1 mol) in toluene (120 mL), alcohol (0.4 mol) was added dropwise in 30 minutes at 0° C. After addition of alcohol, the reaction mixture was heated to 120° C. and stirred for 4 hours until all solid disappeared. The clear solution was allowed to cool to room temperature and solvent was removed under vacuum to yield a greenish oil. The greenish oil was dissolved in 200 mL chloroform, washed with water, brine, dried over $MgSO_4$, and solvent was removed by rotavap. Crude product was further dried under vacuum overnight at room temperature.

Preparation of Alkylphosphorofluoridothioates

Dry $SOF_2$ gas (prepared via refluxing sodium fluoride and thionyl chloride in acetonitrile) was passed through a stirred mixture of O,O-dialkyl dithiophosphoric acid (20 mmol) and triethylamine (30 mmol) in 50 mL anhydrous dichloromethane at −40° C. for 4 hours, then the mixture was allowed to warm up to room temperature for another 4 hours. 30 mL $CH_2Cl_2$ was added to the mixture and then dry $SOF_2$ gas was bubbled through the solution for an additional 1 hour. The mixture was filtered through a gritted glass filter to remove solid residue. The clear solution was washed with saturated $NaHCO_3$ aqueous solution, water, dried over $MgSO_4$, and concentrated under vacuum. Column chromatography purification (silica gel, hexanes) gave alkylphosphorofluoridothioates at yields of 80-90%.

Specific Compounds Synthesized

The following compounds were made using the general procedure above, as demonstrated by the spectral data provided.

| # carbons | Compound Name |
|---|---|
| C4 | n-Butylphosphorofluoridothioate |
| C4 | Iso-Butylphosphorofluoridothioate |
| sec-C4 | 1-Methylpropylphosphorofluoridothioate |
| C5 | 1-Methylbutylphosphorofluoridothioate |
| C6 | 1,3-Dimethylbutylphosphorofluoridothioate |
| C8 | 2-Ethylhexylphosphorofluoridothioate |
| C8 | Octylphosphorofluoridothioate |
| sec-C8 | 1-Methylheptylphosphorofluoridothioate |
| C13 | Tridecylphosphorofluoridothioate |
| sec-C13 | 1-Methyldodecylphosphorofluoridothioate |
| C14 | Tetradecylphosphorofluoridothiate |
| C18 | Octadecylphosphorofluoridothioate |
| C22 | Docosylphosphorofluoridothioate | n-Butylphosphorofluoridothioate

Colorless oil. $^1$H-NMR (500 MHz, $CDCl_3$): 4.20 (t, J=6.4 Hz, 2H), 4.18 (t, J=6.4 Hz, 2H), 1.67-1.73 (m, 4H), 1.39-1.47 (m, 4H), 0.95 (t, J=7.3 Hz, 6H). $^{13}$C-NMR (125 MHz, $CDCl_3$): 69.7 (d, $J_{P-C}$=5.8 Hz), 32.0 (d, $J_{P-C}$=7.2 Hz). $^{19}$F-NMR (470 MHz, $CDCl_3$): −44.5 (d, $J_{P-F}$=1080 Hz). $^{31}$P-NMR (202 MHz, $CDCl_3$): 63.3 (d, $J_{P-F}$=1080 Hz). FT-IR (KBr): 2930, 2852, 1468, 1381, 1016, 878, 648 cm$^{-1}$.

iso-Butylphosphorofluoridothioate

Colorless oil. $^1$H-NMR (500 MHz, $CDCl_3$): 3.96 (d, J=6.9 Hz, 2H), 3.95 (d, J=6.9 Hz, 2H), 1.98-2.03 (m, 2H), 0.97 (d, J=6.9 Hz, 12H). $^{13}$C-NMR (125 MHz, $CDCl_3$): 75.8 (d, $J_{P-C}$=6.2 Hz), 28.9 (d, $J_{P-C}$=7.2 Hz), 18.6. $^{19}$F-NMR (470 MHz, $CDCl_3$): −45.0 (d, $J_{P-F}$=1080 Hz). $^{31}$P-NMR (202 MHz, $CDCl_3$): 63.2 (d, $J_{P-F}$=1080 Hz). FT-IR (KBr): 2967, 2882, 1469, 1396, 1372, 1022, 876, 660 cm$^{-1}$.

1-Methylpropylphosphorofluoridothioate

Colorless oil. $^1$H-NMR (500 MHz, $CDCl_3$): 4.62-4.69 (m, 2H), 1.60-1.75 (m, 4H), 1.36 (d, J=6.4 Hz, 3H), 1.35 (d, J=6.4 Hz, 3H), 0.96 (d, J=7.3 Hz, 6H). $^{13}$C-NMR (125 MHz, $CDCl_3$): 80.3 (d, $J_{P-C}$=5.8 Hz), 80.2 (d, $J_{P-C}$=5.8 Hz), 30.1 (t, $J_{P-C}$=6.7 Hz), 20.8-20.9 (m), 9.5 (d, $J_{P-C}$=5.3 Hz), 9.4. $^{19}$F-NMR (470 MHz, $CDCl_3$): −37.7 (d, $J_{P-F}$=1080 Hz), −38.7 (d, $J_{P-F}$=1080 Hz), −39.6 (d, $J_{P-F}$=1080 Hz). $^{31}$P-NMR (202 MHz, $CDCl_3$): 61.6 (d, $J_{P-F}$=1080 Hz), 61.3 (d, $J_{P-F}$=1080 Hz), 60.9 (d, $J_{P-F}$=1080 Hz). FT-IR (KBr): 2979, 2940, 2882, 1463, 1383, 1175, 1127, 1004, 962, 863, 823, 769, 645 cm$^{-1}$.

1-Methylbutylphosphorofluoridothioate

Colorless oil. ¹H-NMR (500 MHz, CDCl₃): 4.68-4.75 (m, 2H), 1.65-1.73 (m, 2H), 1.50-1.57 (m, 2H), 1.37-1.46 (m, 4H), 1.36 (d, J=6.4 Hz, 3H), 1.35 ((d, J=6.4 Hz, 3H), 0.94 (t, J=7.3 Hz, 6H). ¹³C-NMR (125 MHz, CDCl₃): 79.0 (d, $J_{P-C}$=6.2 Hz), 78.8 (t, $J_{P-C}$=5.3 Hz), 39.3-39.4 (m), 21.4, 18.5 (d, $J_{P-C}$=3.4 Hz), 18.4, 13.8. ¹⁹F-NMR (470 MHz, CDCl₃): −37.3 (d, $J_{P-F}$=1080 Hz), −38.5, (d, $J_{P-F}$=1080 Hz), −39.5 (d, $J_{P-F}$=1080 Hz). ³¹P-NMR (202 MHz, CDCl₃): 61.7 (d, $J_{P-F}$=1080 Hz), 61.3 (d, $J_{P-F}$=1080 Hz), 60.9 (d, $J_{P-F}$=1080 Hz). FT-IR (KBr): 2963, 2937, 2876, 1463, 1383, 1170, 1123, 1006, 878, 812, 743, 641 cm⁻¹.

1,3-Dimethylbutylphosphorofluoridothioate

¹H-NMR (500 MHz, CDCl₃): 4.74-4.81 (m, 2H), 1.64-1.76 (m, 4H), 1.34-1.37 (m, 8H), 0.91-0.95 (m, 12H). ¹³C-NMR (125 MHz, CDCl₃): 77.6 (d, $J_{P-C}$=5.8 Hz), 77.5 (t, $J_{P-C}$=9.1 Hz), 46.4-46.5 (m), 24.5, 24.1 (d, $J_{P-C}$=1.9 Hz), 22.9-23.0 (m), 22.1-22.2 (m), 21.9. ¹⁹F-NMR (470 MHz, CDCl₃): −36.3 (d, $J_{P-F}$=1080 Hz), −37.9 (d, $J_{P-F}$=1080 Hz), −39.3 (d, $J_{P-F}$=1080 Hz). ³¹P-NMR (202 MHz, CDCl₃): 61.8 (d, $J_{P-F}$=1080 Hz), 61.3 (d, $J_{P-F}$=1080 Hz), 60.7 (d, $J_{P-F}$=1080 Hz). FT-IR (KBr): 2960, 2873, 1470, 1383, 1298, 1162, 1124, 995, 876, 802, 634, 507 cm⁻¹.

2-Ethylhexylphosphorofluoridothioate

¹H-NMR (500 MHz, CDCl₃): 4.05-4.11 (m, 4H), 1.59-1.63 (m, 2H), 1.29-1.42 (m, 16H), 0.89-0.92 (m, 12H). ¹³C-NMR (125 MHz, CDCl₃): 70.7 (d, $J_{P-C}$=7.2 Hz), 70.2 (d, $J_{P-C}$=8.2 Hz), 39.9 (d, $J_{P-C}$=8.6 Hz), 30.1 (m), 29.0, 23.5 (d, $J_{P-C}$=9.1 Hz), 23.1 (d, $J_{P-C}$=6.2 Hz), 14.2 (d, $J_{P-C}$=5.3 Hz), 11.1. ¹⁹F-NMR (470 MHz, CDCl₃): −45.0 (d, $J_{P-F}$=1080 Hz), −45.1 (d, $J_{P-F}$=1080 Hz), −45.1 (d, $J_{P-F}$=1080 Hz). ³¹P-NMR (202 MHz, CDCl₃): 63.6 (d, $J_{P-F}$=1080 Hz). FT-IR (KBr): 2962, 2932, 2862, 1463, 1381, 1021, 882, 728, 662 cm⁻¹.

Octylphosphorofluoridothioate

¹H-NMR (500 MHz, CDCl₃): 4.19 (t, J=6.9 Hz, 2H), 4.17 (t, J=6.9 Hz, 2H), 1.68-1.74 (m, 4H), 1.27-1.41 (m, 20H), 0.89 (t, J=6.9 Hz, 6H). ¹³C-NMR (125 MHz, CDCl₃): 70.0 (d, $J_{P-C}$=5.8 Hz), 31.8, 30.0 (d, $J_{P-C}$=7.2 Hz), 29.1 (d, $J_{P-C}$=12.0 Hz), 25.4, 22.7, 14.1. ¹⁹F-NMR (470 MHz, CDCl₃): −44.4 (d, $J_{P-F}$=1080 Hz). ³¹P-NMR (202 MHz, CDCl₃): 63.3 (d, $J_{P-F}$=1080 Hz). FT-IR (KBr): 2928, 2857, 1466, 1379, 1018, 883, 723, 642 cm⁻¹.

1-Methylheptylphosphorofluoridothioate

¹H-NMR (500 MHz, CDCl₃): 4.68-4.73 (m, 2H), 1.66-1.72 (m, 2H), 1.52-1.58 (m, 2H), 1.28-1.39 (m, 22H), 0.89 (t, J=7.2 Hz, 6H). ¹³C-NMR (125 MHz, CDCl₃): 79.2 (d, $J_{P-C}$=5.8 Hz), 79.1 (t, $J_{P-C}$=5.3 Hz), 37.2-37.3 (m), 31.8 (d, $J_{P-C}$=2.4 Hz), 31.7, 29.0-29.1 (m), 25.2 (d, $J_{P-C}$=2.4 Hz), 25.0 (d, $J_{P-C}$=2.4 Hz), 22.6, 21.4, 14.1. ¹⁹F-NMR (470 MHz, CDCl₃): −37.2 (d, $J_{P-F}$=1080 Hz), −38.4 (d, $J_{P-F}$=1080 Hz), −39.5 (d, $J_{P-F}$=1080 Hz). ³¹P-NMR (202 MHz, CDCl₃): 61.7 (d, $J_{P-F}$=1080 Hz), 61.3 (d, $J_{P-F}$=1080 Hz), 60.8 (d, $J_{P-F}$=1080 Hz). FT-IR (KBr): 2932, 2839, 1463, 1382, 1126, 1002, 878, 824, 641 cm⁻¹.

Tridecylphosphorofluoridothioate

Pale yellow oil. ¹H-NMR (500 MHz, CDCl₃): 4.18 (t, J=6.9 Hz, 2H), 4.16 (t, J=6.9 Hz, 2H), 1.68-1.73 (m, 4H), 1.23-1.39 (m, 40H), 0.88 (t, J=6.9 Hz, 6H). ¹³C-NMR (125 MHz, CDCl₃): 70.0 (d, $J_{P-C}$=5.8 Hz), 32.0, 30.0 (d, $J_{P-C}$=7.2 Hz), 29.8, 29.7, 29.6, 29.5, 29.4, 29.2, 25.4, 22.8, 14.2. ¹⁹F-NMR (470 MHz, CDCl₃): −44.3 (d, $J_{P-F}$=1080 Hz). ³¹P-NMR (202 MHz, CDCl₃): 63.3 (d, $J_{P-F}$=1080 Hz). FT-IR (KBr): 2925, 2854, 1466, 1378, 1016, 885, 722, 643 cm⁻¹. HRMS: MH⁺ 481.3631, expected 481.3639. ESI-TOF results were as expected.

1-Methyldodecylphosphorofluoridothioate

Colorless oil. $^1$H-NMR (500 MHz, CDCl$_3$): 4.67-4.73 (m, 2H), 1.66-1.70 (m, 2H), 1.52-1.57 (m, 2H), 1.23-1.37 (m, 42H), 0.88 (t, J=6.9 Hz, 6H). $^{13}$C-NMR (125 MHz, CDCl$_3$): 79.1 (d, $J_{P-C}$=6.2 Hz), 79.0 (t, $J_{P-C}$=5.3 Hz), 37.2-37.3 (m), 32.0, 29.4-29.8 (m), 25.2 (d, $J_{P-C}$=3.4 Hz), 25.1 (d, $J_{P-C}$=2.4 Hz), 22.8, 21.4, 14.7. $^{19}$F-NMR (470 MHz, CDCl$_3$): −37.3 (d, $J_{P-F}$=1080 Hz), −38.5 (d, $J_{P-F}$=1080 Hz), −39.5 (d, $J_{P-F}$=1080 Hz). $^{31}$P-NMR (202 MHz, CDCl$_3$): 61.7 (d, $J_{P-F}$=1080 Hz), 61.3 (d, $J_{P-F}$=1080 Hz), 60.8 (d, $J_{P-F}$=1080 Hz). FT-IR (KBr): 2926, 2855, 1465, 1382, 1126, 1001, 879. 722, 643 cm$^{-1}$. HRMS: MNa$^+$ 503.3450, expected 503.3458. ESI-TOF results were as expected.

Tetradecylphosphorofluoridothiate

Colorless oil. $^1$H-NMR (500 MHz, CDCl$_3$): 4.18 (t, J=6.4 Hz, 2H), 4.16 (t, J=6.4 Hz, 2H), 1.67-1.73 (m, 4H), 1.22-1.39 (m, 44H), 0.88 (t, J=7.3 Hz, 6H). $^{13}$C-NMR (125 MHz, CDCl$_3$): 70.1 (d, $J_{P-C}$=5.8 Hz), 32.0, 30.0 (d, $J_{P-C}$=7.2 Hz), 29.7-29.8 (m), 29.6, 29.5, 29.4, 29.2, 25.4, 22.8, 14.2. $^{19}$F-NMR (470 MHz, CDCl$_3$): −44.3 (d, $J_{P-F}$=1080 Hz). $^{31}$P-NMR (202 MHz, CDCl$_3$): 63.3 (d, $J_{P-F}$=1080 Hz). FT-IR (KBr): 2923, 2854, 1469, 1382, 1126, 1012, 886, 722, 646 cm$^{-1}$.

Octadecylphosphorofluoridothioate

Colorless solid, yield, melting point: 36-37° C. $^1$H-NMR (500 MHz, CDCl$_3$): 4.18 (t, J=6.4 Hz, 2H), 4.16 (t, J=6.4 Hz, 2H), 1.67-1.73 (m, 4H), 1.25-1.38 (m, 60H), 0.88 (t, J=7.3 Hz, 6H). $^{13}$C-NMR (125 MHz, CDCl$_3$): 70.0 (d, $J_{P-C}$=5.8 Hz), 32.0, 30.0 (d, $J_{P-C}$=7.2 Hz), 29.6-29.7 (m), 29.6, 29.5, 29.4, 29.1, 25.4, 22.7, 14.1. $^{19}$F-NMR (470 MHz, CDCl$_3$): −44.3 (d, $J_{P-F}$=1080 Hz). $^{31}$P-NMR (202 MHz, CDCl$_3$): 63.3 (d, $J_{P-F}$=1080 Hz). FT-IR (KBr): 2921, 2851, 1471, 1377, 1026, 869, 719, 653 cm$^{-1}$. HRMS: MNa$^+$ 643.5017, expected 643.5023. ESI-TOF results were as expected.

Docosylphosphorofluoridothioate

Colorless solid, yield, melting point: 51-52° C. $^1$H-NMR (500 MHz, CDCl$_3$): 4.18 (t, J=6.4 Hz, 2H), 4.16 (t, J=6.4 Hz, 2H), 1.68-1.73 (m, 4H), 1.25-1.39 (m, 76H), 0.88 (t, J=7.3 Hz, 6H). $^{13}$C-NMR (125 MHz, CDCl$_3$): 70.1 (d, $J_{P-C}$=5.8 Hz), 32.0, 30.0 (d, $J_{P-C}$=7.2 Hz), 29.7-29.8 (m), 29.6, 29.5, 29.4, 29.2, 25.4, 22.8, 14.2. $^{19}$F-NMR (470 MHz, CDCl$_3$): −44.3 (d, $J_{P-F}$=1080 Hz). $^{31}$P-NMR (202 MHz, CDCl$_3$): 63.3 (d, $J_{P-F}$=1080 Hz). FT-IR (KBr): 2919, 2851, 1469, 1382, 1019, 878, 797, 721, 645 cm$^{-1}$.

EXAMPLE 2

Tribological Testing of Alkylphosphorofluoridothioates

All compounds were diluted in 100 N base oil to a phosphorus concentration of 0.1 wt % and tribological tests were conducted in a High Frequency Reciprocating Ball on Stationary Flat tribometer. The ball and the flat were both made of 52100 steel and were immersed in the oil mixture. The test temperature was 100° C., the load applied on the ball was 1.0 Kg, the frequency of the test was 50 Hz, and the duration of the test was 1 hour. Wear volume was measured by Vecco Wyko NT9100 Optical Profiler System with Vision®. XANES (X-ray Absorption Near Edge Structure) was obtained at Canadian Light Source, Saskatoon, SK, Canada. After the completion of the test, the flat sample was cleaned and the amount of material that was removed by wear was measured using an optical profilometer.

Wear Volume Results

Figure 1:
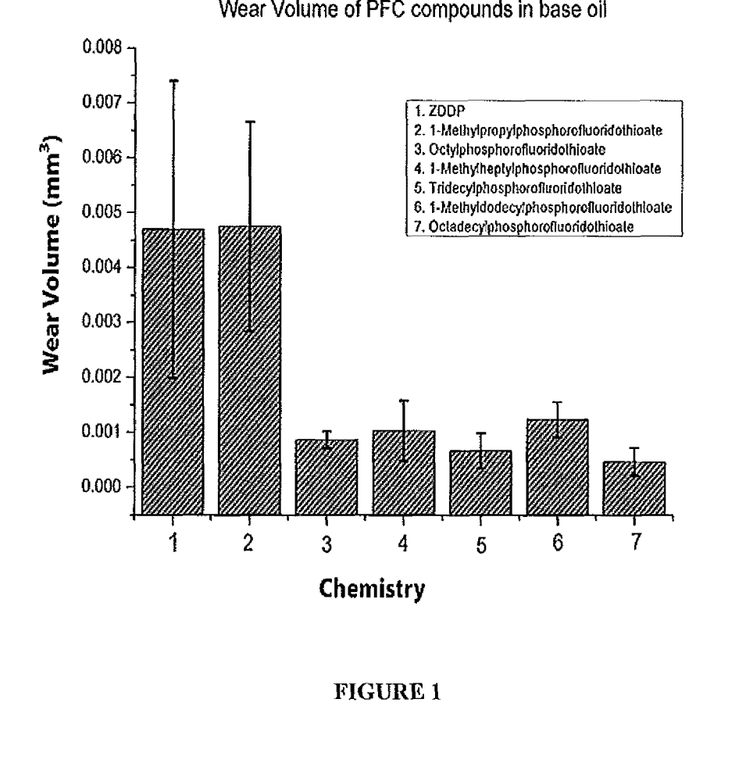
FIG. 1 illustrates the results of tribological tests for different alkylphosphorofluoridothioates in base oil. ZDDP is shown in Lane 1 for comparison.

FIG. 1 shows the wear volume for the compounds shown in Table 1, including ZDDP for reference in lane 1. The compound illustrated by lane 2 has alkyl groups of 4 carbons and demonstrates no better wear volume than ZDDP. However, the other compounds, having alkyl groups from 8 to 18 carbons, have significantly lower wear volumes compared to ZDDP at equivalent levels of phosphorous.

| Lane | Compound | # of carbons in alkyl groups |
| --- | --- | --- |
| 1 | ZDDP | |
| 2 | 1-Methylpropylphosphorofluoridothioate | 4 |
| 3 | Octylphosphorofluoridothioate | 8 |
| 4 | 1-Methylheptylphosphorofluoridothioate | 8 |
| 5 | Tridecylphosphorofluoridothioate | 13 |
| 6 | 1-Methyldodecylphosphorofluoridothioate | 13 |
| 7 | Octadecylphosphorofluoridothioate | 18 |

XANES Results

X-ray absorption near-edge structure (XANES) was used to determine the nature of the tribofilm that formed in the tests described above. L-edge XANES focuses on the top 20-40 nm of the surface whereas K-edge focuses on 100-150 nm within the surface.

Figure 2:
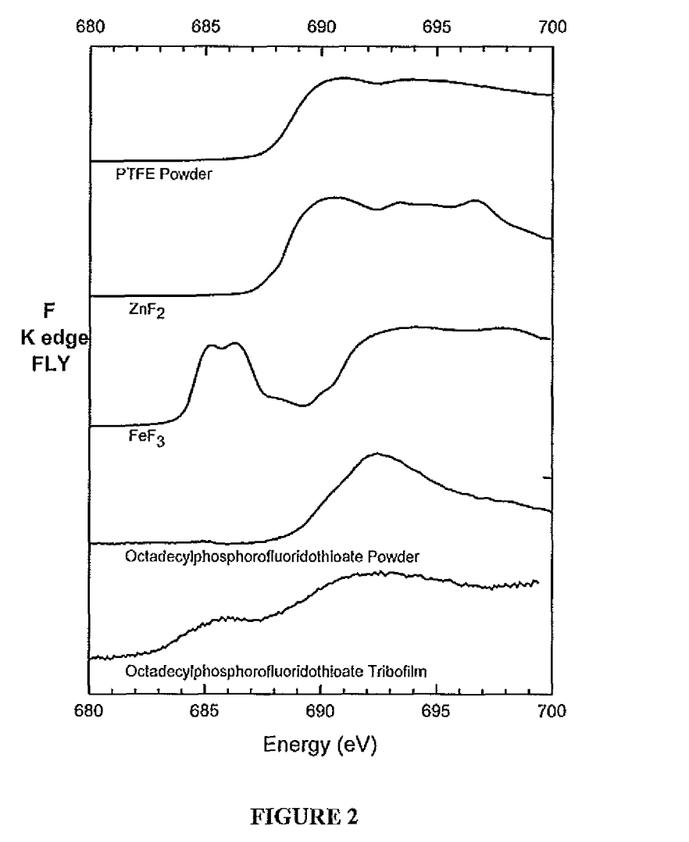
FIG. 2 illustrates the fluorescence yield (FLY) fluorine K-edge XANES spectra of fluorine containing model compounds, C18 (octadecylphosphorofluoridothioate) powder, and a tribofilm of the C18 compound.
Figure 3:
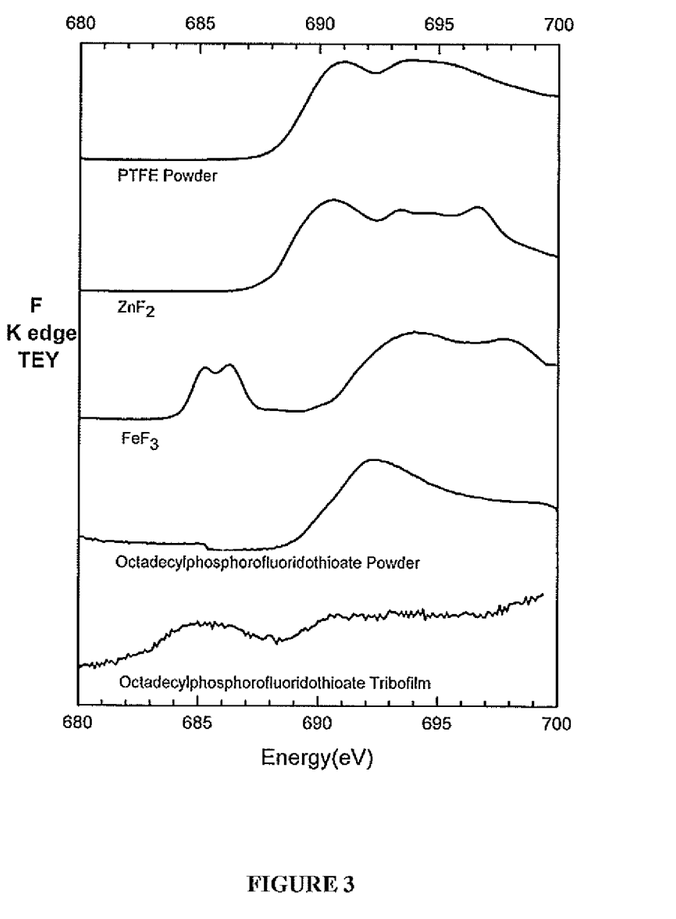
FIG. 3 illustrates the total electron yield (TEY) fluorine K-edge XANES spectra of fluorine containing model compounds, C18 powder, and a tribofilm of the C18 compound.

FIGS. 2 and 3 show the fluoride K-edge XANES for various compounds taken in fluorescence yield (FLY) (FIG. 2) and total electron yield (TEY) (FIG. 3). The compounds are PTFE, zinc fluoride, iron fluoride, C18 powder, and C18 tribofilm. The figures show that the C18 tribofilm contains iron fluoride in addition to polytetrafluoroethylene (PTFE). The PTFE is created in-situ during tribological testing. When the alkylphosphorofluoridothioates decompose under tribological conditions they react with the substrate leading to the formation of FeF$_3$ as well as PTFE. This is beneficial because PTFE is known to reduce friction and FeF$_3$ being very polar helps in the adhesion of the tribofilm to the surface. The TEY provides information from the top 10 nm of the tribofilm while the FLY provides information from up to 100 nm into the tribofilm. Hence, FIG. 2 also illustrates that the effect is deeper into the tribofilm.

Figure 4:
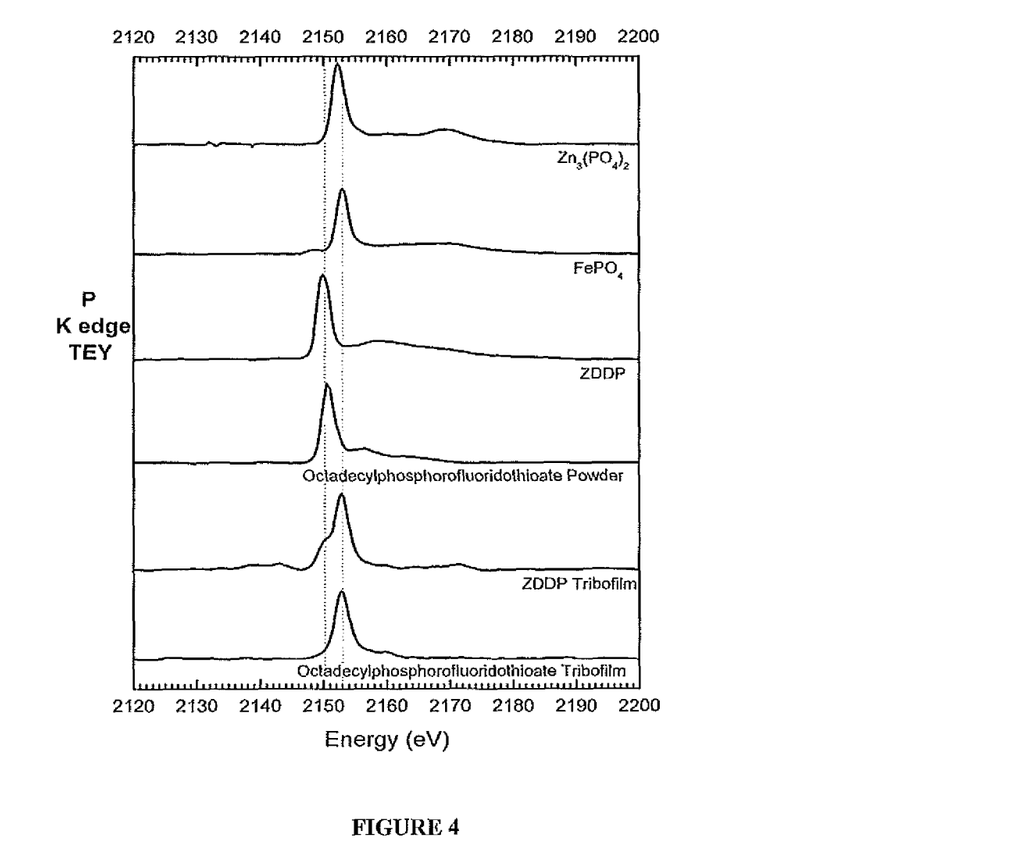
FIG. 4 illustrates the TEY phosphorus K-edge XANES spectra of phosphorus containing model compounds, ZDDP, ZDDP tribofilm, C18 powder, and a tribofilm of the C18 compound.

FIG. 4 shows the phosphorous K-edge XANES for various compounds taken in total electron yield (TEY). The peak at 2150 eV indicates the presence of zinc phosphate while the peak at 2153 eV indicates iron phosphate. ZDDP contains zinc in its structure while C18 does not, however, both tribofilms indicate the presence of iron phosphate with iron being contributed by reaction of the additives with the steel substrate.

Figure 5:
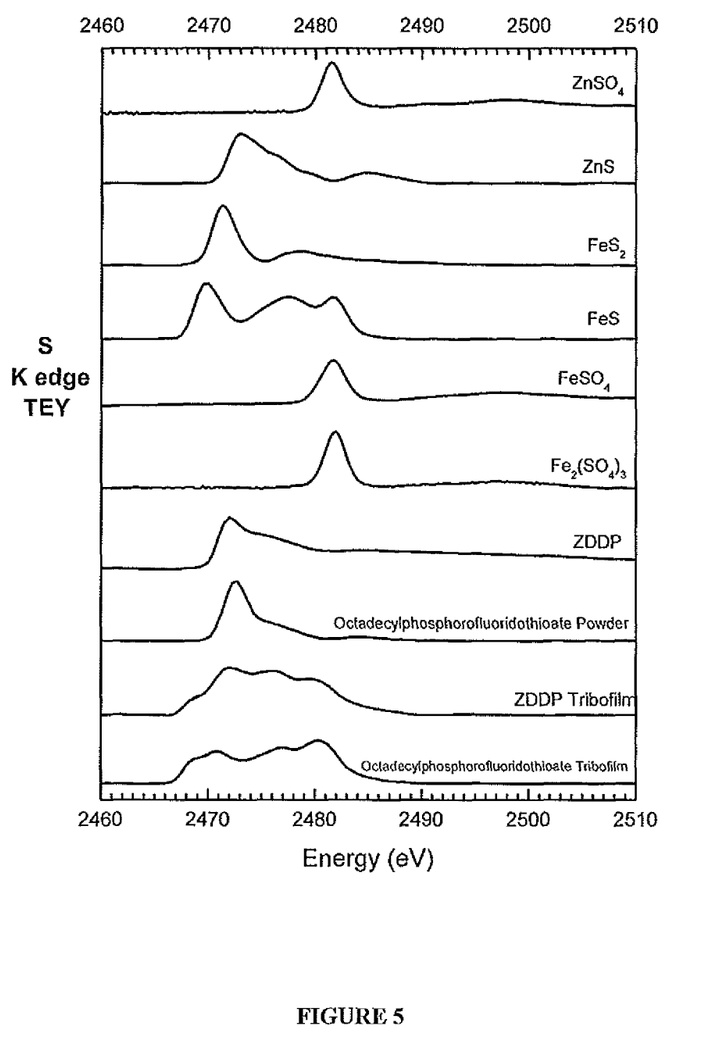
FIG. 5 illustrates the TEY sulfur K-edge XANES spectra of sulfide and sulfate containing model compounds, ZDDP, ZDDP tribofilm, C18 powder, and a tribofilm of the C18 compound.

FIG. 5 shows the sulfur K-edge XANES for various compounds taken in total electron yield (TEY). The top 6 spectra are for various iron and zinc sulfides and sulfates. Iron and zinc sulfides have peaks near 2473 eV while iron and zinc sulfates have peaks near 2481 eV. The bottom 4 spectra are for ZDDP, C18 powder, ZDDP tribofilm, and C18 tribofilm. This Figure shows that ZDDP tribofilm has about equal mixture of sulfates and sulfides but C18 tribofilm has a larger fraction of sulfides. It is well known that sulfates, which are in the oxidized state, are much more abrasive in comparison to sulfides, which are in the reduced state. The sulfides can be sheared and provide wear protection while the sulfates are harder and tend to be abrasive in nature.

Figure 6:
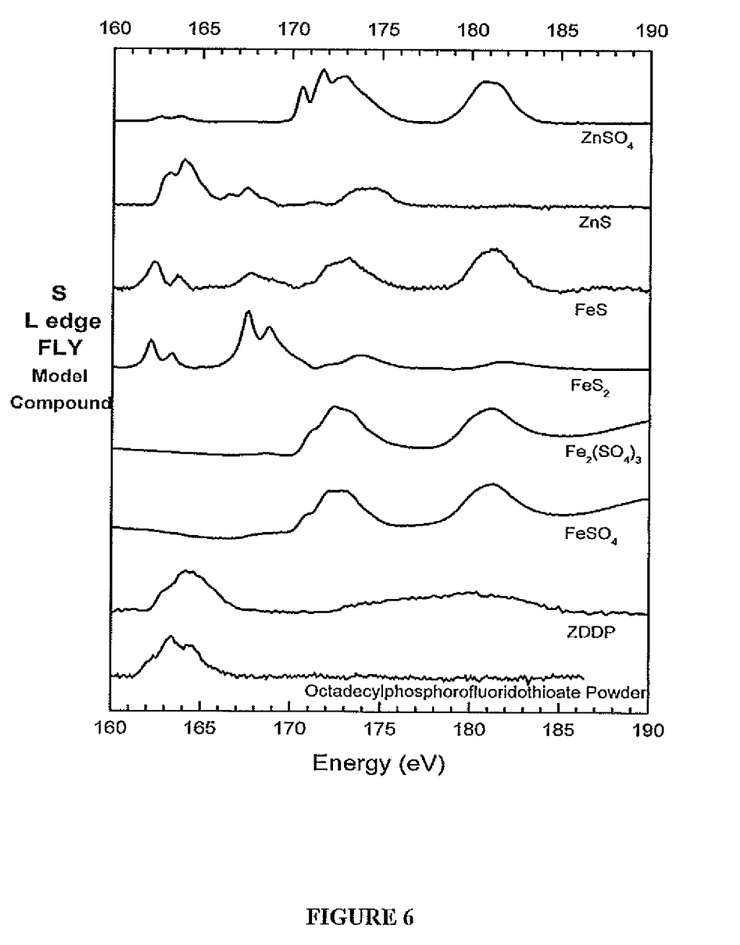
FIG. 6 illustrates the FLY sulfur L-edge XANES spectra of sulfur containing model compounds, C18 powder, and ZDDP.
Figure 7:
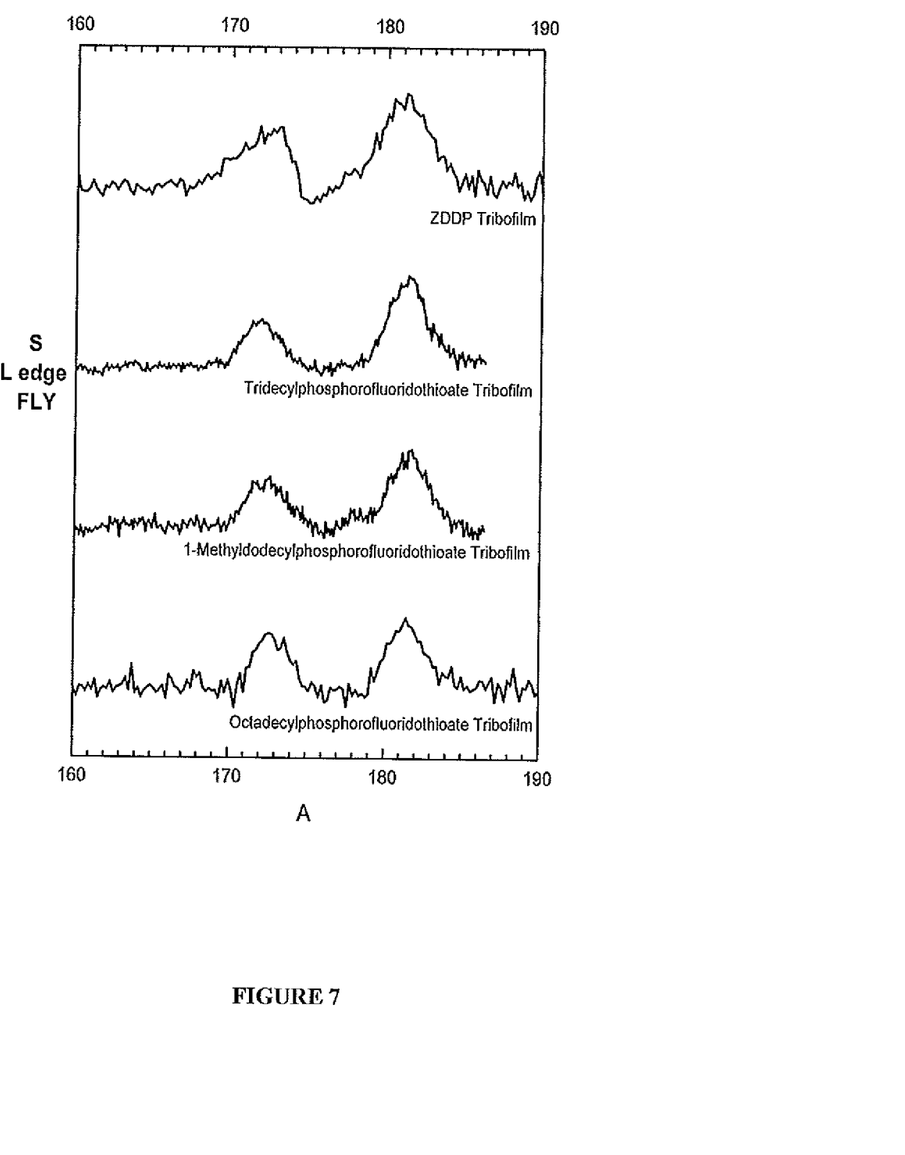
FIG. 7 illustrates the FLY sulfur L-edge XANES spectra of tribofilms of ZDDP, tridecylphosphorofluoridothioate (C13), 1-methyldodecylphosphorofluoridothioate (C13S), and C18.

FIGS. 6 and 7 illustrate sulfur L-edge XANES in FLY. FIG. 6 illustrates spectra from several model compounds of sulfides and sulfates as well as ZDDP and C18. FIG. 7 illustrates the spectra from tribofilms of ZDDP, tridecylphosphorofluoridothioate (C13), 1-methyldodecylphosphorofluoridothioate (C13S), and C18. The L-edge spectra provides information from the very top of the tribofilm near the top 30-40 nm and indicates that in all cases the very top of the tribofilms are made up of sulfates which is not surprising as the surface is oxidized easily.

Figure 8:
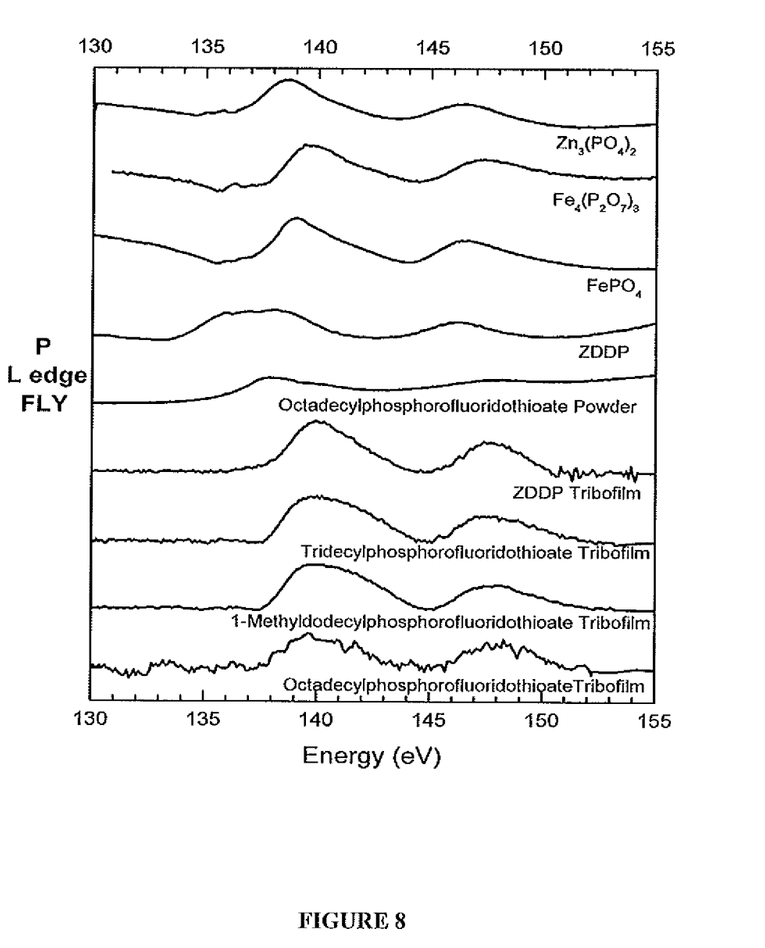
FIG. 8 illustrates the FLY phosphorus L-edge XANES spectra of phosphorous containing model compounds, ZDDP, C18, and tribofilms of ZDDP, tridecylphosphorofluoridothioate (C13), 1-methyldodecylphosphorofluoridothioate (C13S), and C18.

FIG. 8 illustrates the FLY phosphorus L-edge spectra of phosphate standards, ZDDP, C18 and tribofilms of ZDDP, tridecylphosphorofluoridothioate (C13), 1-methyldodecylphosphorofluoridothioate (C13S), and C18. The spectra indicate the formation of iron phosphates in all cases which are protective of the surface. The L-edge spectra also provide information from the top 30-40 nm of the tribofilm.

EXAMPLE 3

Thermal Stability

Figure 9:
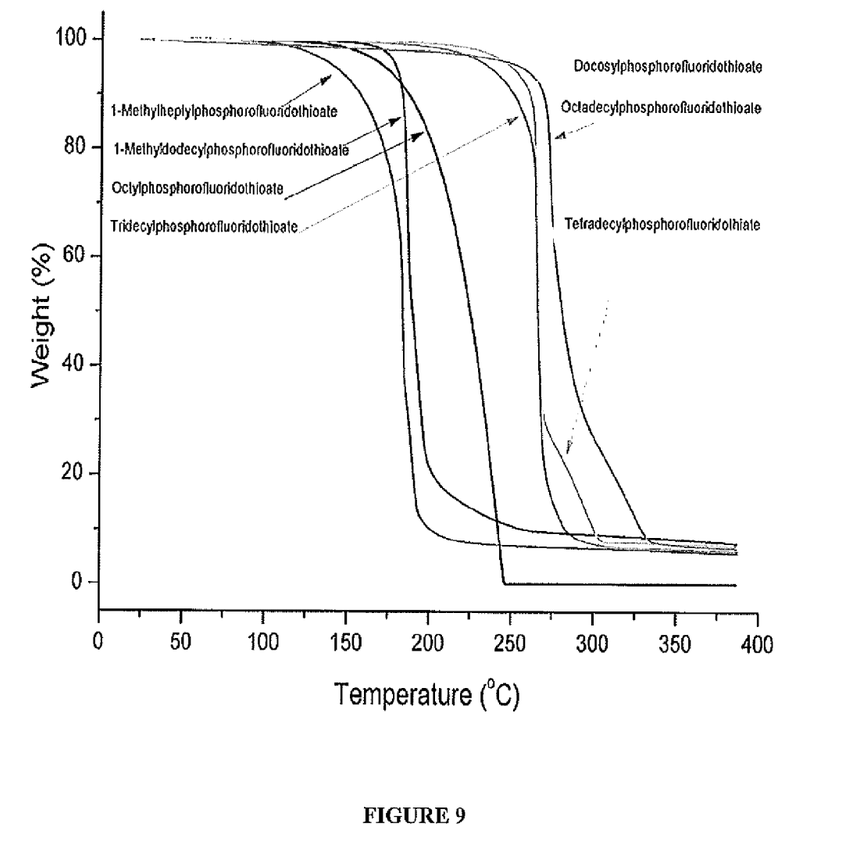
FIG. 9 illustrates the thermal stability of different alkylphosphorofluoridothioates.

Thermal stability of the alkylphosphorofluoridothioates was examined using a Thermogravimetric Analyzer (TGA) to examine the decomposition temperature. FIG. 9 shows the change in weight of different alkylphosphorofluoridothioates as a function of temperature when they were heated in the TGA in an environment of argon at a heating rate of 5° C. per minute. The alkylphosphorofluoridothioates made with primary alcohols are more stable than the ones made from secondary alcohols. In addition, the alkylphosphorofluoridothioates with longer chain alkyl groups are more stable than ones with shorter chain alkyl groups.

The various thermal stabilities of the compounds mean that there is quite a bit of capability to tailor the operative temperature range in which wear protection can be achieved as well as length of time for the wear protection (time-temperature profiles for wear protection). This flexibility comes from both the chemical structure of the compounds as well as the capability to use mixtures of compounds, for example low temperature decomposition materials for early wear protection mixed with higher temperature decomposition materials for longer time wear protection.

EXAMPLE 4

Mixtures of Alkylphosphorofluoridothioates and Zddp

Figure 10:
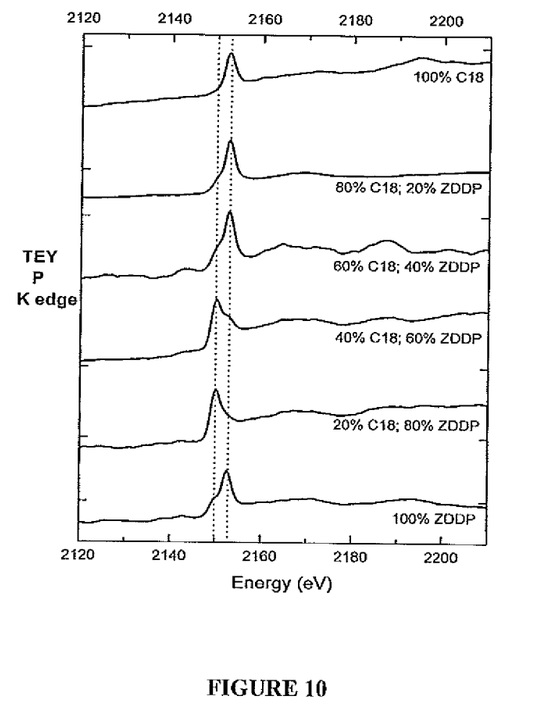
FIG. 10 illustrates the TEY phosphorous K-edge XANES spectra of tribofilms from ZDDP and C18 and different mixtures of the two compounds.

Mixtures of the alkylphosphorofluoridothioate octadecylphosphorofluoridothioate (C18) with ZDDP at 20%, 40%, 60%, and 80% C18 were made. The mixtures were diluted in mineral base oil to yield a nominal composition of 0.1 wt % of phosphorous in all the mixtures. These compositions were wear tested for 1 hour in a High Frequency Reciprocating Ball (HFRB) at a load of 1 kg and a temperature of 100° C. The wear surfaces formed from these wear tests were examined using XANES. FIG. 10 shows the phosphorous K-edge XANES spectra of wear surfaces taken in total electron yield mode. The peak at 2150 eV indicates the presence of zinc phosphate $Zn_3(PO_4)_2$ while the peak at 2153 eV indicates iron phosphate $FePO_4$. The data shows that when 100% ZDDP is used the tribofilm is actually made up of iron phosphate which is the same as when 100% C18 is used. However, the mixtures having 20% and 40% C18 generated zinc phosphate which is beneficial from a wear point of view as compared to iron phosphate.

Figure 11:
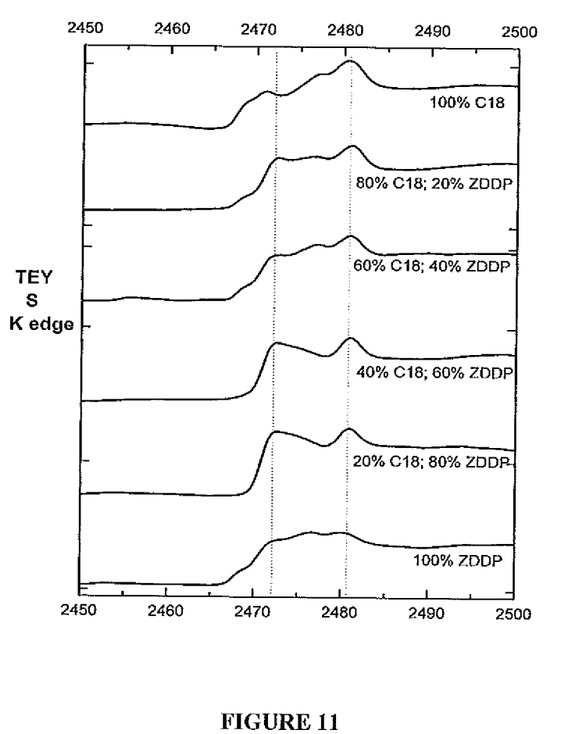
FIG. 11 illustrates the TEY sulfur K-edge XANES spectra of tribofilms from ZDDP and C18 and different mixtures of the two compounds.

FIG. 11 is sulfur K-edge XANES spectra of wear surface for the different mixtures of additives taken in total electron yield. The peaks near the dotted line at 2473 eV indicate the presence of iron and zinc sulfides while the peaks near the dotted line at 2481 eV indicate iron and zinc sulfates. The figure shows that when 100% ZDDP is used the tribofilm is made up of an equal mixture of sulfates and sulfides of Fe and Zn. It is well known that the presence of sulfides is beneficial for wear as opposed to sulfates. When a mix of 20% C18 with 80% ZDDP is considered there are still sulfides and sulfates, however there is a larger fraction of sulfides-indicating a better wear performance in comparison to 100% ZDDP.

Both the phosphorous K-edge and sulfur K-edge data clearly show that even having a small proportion of C18 significantly improves wear performance.

Modifications and variations of the present invention will be apparent to those skilled in the art from the forgoing detailed description. All modifications and variations are intended to be encompassed by the following claims. All publications, patents, and patent applications cited herein are hereby incorporated by reference in their entirety.

What is claimed is:

1. A method for synthesizing an alkylphosphorofluoridothioate having desired alkyl groups, comprising the steps:
   i) reacting phosphorus pentasulfide with alcohol having the desired alkyl groups to form an O,O-dialkyl dithiophosphoric acid; and
   ii) reacting the O,O-dialkyl dithiophosphoric acid with thionyl fluoride ($SOF_2$) so that one of the thio groups is replaced by a fluoride to yield the alkylphosphorofluoridothioate.

2. A pure alkylphosphorofluoridothioate having the structure wherein $R_1$ and $R_2$ are the same or different and are alkyl groups with between 5 and 40 carbons.

3. The alkylphosphorofluoridothioate of claim 2 wherein $R_1$ and $R_2$ are alkyl groups with between 5 and 22 carbons.

4. A lubricant additive comprising a pure alkylphosphorofluoridothioate having the structure wherein $R_1$ and $R_2$ are the same or different and are alkyl groups with between 5 and 40 carbons.

5. The lubricant additive of claim 4, wherein $R_1$ and $R_2$ are alkyl groups with between 5 and 22 carbons.

6. A lubricant comprising a lubricant base and a lubricant additive of claim 4.

7. The lubricant of claim 6 further comprising one or more additional alkylphosphorofluoridothioates having the structure wherein $R_1$ and $R_2$ are the same or different and are alkyl groups with between 5 and 40 carbons.

8. The lubricant of claim 6 wherein $R_1$ and $R_2$ are alkyl groups with between 5 and 22 carbons.

9. The lubricant of claim 6 wherein the lubricant exhibits a wear volume less than a similarly formulated lubricant containing ZDDP, normalized for the same phosphorus amount.

10. The lubricant of claim 6 further comprising additional additives selected from additional antiwear compounds, detergents, dispersants, antioxidants, pour point depressants, viscosity modifiers, corrosion inhibitors, and combinations thereof.

11. The lubricant of claim 10, wherein the additional antiwear compound is selected from organophosphates such as zinc dialkyldithiophosphate (ZDDP), organofluorine compounds such as polytetrafluoroethylene (PTFE), ashless phosphates, ashless thiophosphates, and combinations thereof.

12. The lubricant of claim 11 wherein the alkylphosphorofluoridothioate comprises between 5 and 50% of the total antiwear compounds in the lubricant.

13. The lubricant of claim 8 wherein the lubricant is a motor oil, wherein the lubricant base is a base oil, and wherein the amount of alkylphosphorofluoridothioate in the lubricant is the amount that provides a phosphorous concentration of from about 0.01 to 0.15 wt % phosphorous.

14. The lubricant of claim 6 wherein the lubricant is a grease, wherein the lubricant base is a mixture of mineral oil and soap thickener, and wherein the amount of alkylphosphorofluoridothioate in the lubricant is the amount that provides a phosphorous concentration of from about 0.01 to 0.5 wt % phosphorous.

15. The lubricant of claim 6 wherein the lubricant is a gear oil or transmission oil and wherein the amount of alkylphosphorofluoridothioate in the lubricant is the amount that provides a phosphorous concentration of from about 0.01 to 0.3 wt % phosphorous.

16. The lubricant of claim 7 comprising at least two alkylphosphorofluoridothioates having different temperature decomposition profiles.

17. A lubricant additive comprising a pure alkylphosphorofluoridothioate having the structure wherein $R_1$ and $R_2$ are the same or different and are alkyl groups with between 5 and 22 carbons and
wherein the additive provides lubricant having a lower wear volume than a similarly formulated lubricant containing ZDDP at an equivalent weight percentage of phosphorus.

* * * * *